United States Patent [19]

Wertheimer et al.

[11] Patent Number: 4,786,399
[45] Date of Patent: Nov. 22, 1988

[54] SEAL MEANS FOR ISOLATED GROUNDED $O_2$ SENSOR

[75] Inventors: Harry P. Wertheimer, Findlay; David C. Weber, Toledo, both of Ohio

[73] Assignee: Allied-Signal Inc., Morristown, N.J.

[21] Appl. No.: 102,056

[22] Filed: Sep. 28, 1987

[51] Int. Cl.[4] .............................................. G01N 27/46
[52] U.S. Cl. ................................. 204/427; 204/424; 204/428
[58] Field of Search ........................ 204/1 S, 421–429

[56] References Cited

U.S. PATENT DOCUMENTS

| | | | |
|---|---|---|---|
| 3,720,594 | 3/1973 | Wilson | 204/427 |
| 4,247,380 | 1/1981 | McIntyre | 204/1 S |
| 4,597,849 | 7/1986 | Burkhardt et al. | 204/427 |
| 4,717,464 | 1/1988 | Oshima et al. | 204/428 |

Primary Examiner—T. Tung
Attorney, Agent, or Firm—Leo H. McCormick, Jr.; Ken C. Decker

[57] ABSTRACT

A sensor (24) having a metal shell (30) joined to a sleeve (96) to locate a heater (92) in a thimble of an electrolyte member (72). A sealed joint is produced between the sleeve (96) and metal shell (30) to define a sealed reference chamber (118). A porous filter (112) in the sleeve (96) prevents water in environmental air from entering the reference chamber (118). Leads (106') and (106") which pass through a seal (123) adjacent the porous filter (112) are connected to terminals (164 and 164'). Terminals (164 and 164') located in a terminal member (120) position a heater (92) within chamber (118) and the electrolyte member (72). Leads (106 and 106") which pass through the porous filter are connected to contact rings (142 and 144). Contact rings (142 and 144) are connected to an external and internal coating (80 and 82) on the electrolyte member (72). In response to a signal from a controller (26) electrical current is supplied to the heater (92) to maintain the temperature in chamber (118) above present limits such that changes in the ion conduction through the electrolyte member (72) is accurately measured. The changes result from a difference in the oxygen content of air in the reference chamber (118) as compared with oxygen in an exhaust gas supplied to the external surface (80). The seal (123) and filter (112) are free to move axially within the sleeve (96) while still maintaining radial engagement to assure that only dry environmental air is presented to the reference chamber (18).

5 Claims, 3 Drawing Sheets

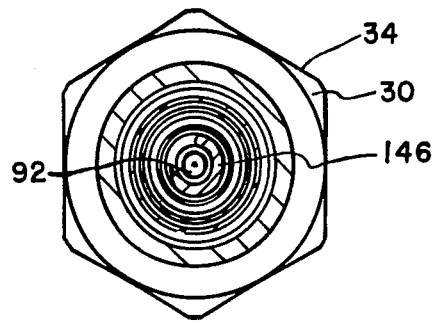
FIG. 5
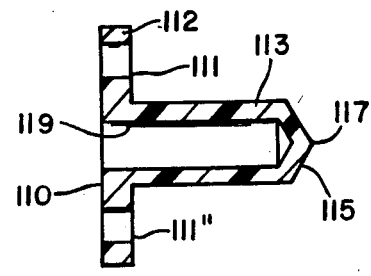
FIG. 14
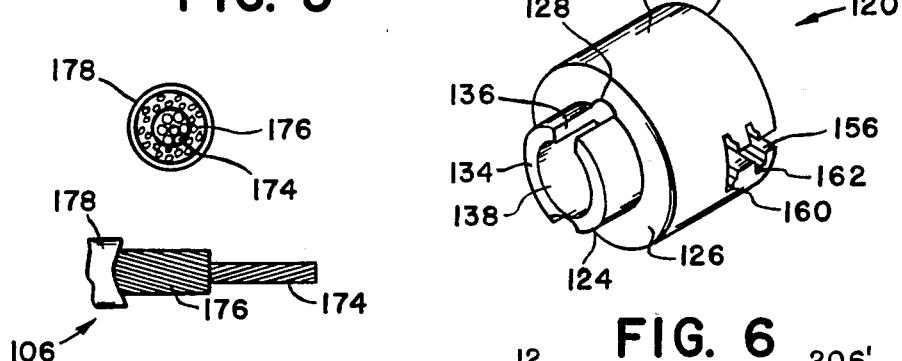
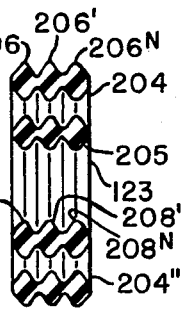
FIG. 6
FIG. 9
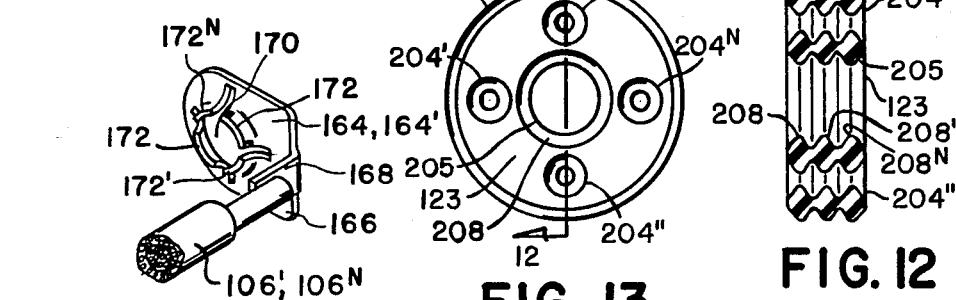
FIG. 7      FIG. 13      FIG. 12
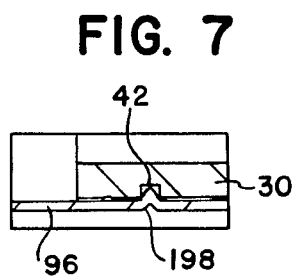
FIG. 11
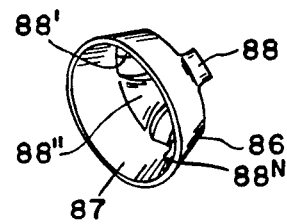
FIG. 8

SEAL MEANS FOR ISOLATED GROUNDED O₂ SENSOR

BACKGROUND OF THE INVENTION

1. Field of the Invention

The present invention is related to a gas constituent electrochemical sensor for sensing the concentration of oxygen in an unknown gas relative to a reference gas. This sensor has a tubular electrolyte thimble with an internal and external conductive coating connected to a control member. Changes in oxygen concentration in the gas as compared to the reference concentration creates an operational signal indicative of air/fuel ratio supplied to an engine. A seal assembly prevents water or other liquids from being communicated to the sensor. A heater member receives electrical current from the control member to maintain the temperature of the thimble above a minimum operational temperature. As a result, the operational signal is only dependent on the difference in the oxygen concentration between the unknown and reference gases.

2. Description of the Prior Art

It is known that a body of solid electrolyte, for example zirconium dioxide, which has one surface exposed to a reference oxygen concentration and a second surface exposed to an unknown oxygen concentration may generate an electrical potential between such surfaces. Examples of sensors which use such an electrolyte member may be found in U.S. Pat. Nos. 3,960,692 and 3,960,693, which issued June 1, 1976, U.S. Pat. No. 4,019,974 which issued Apr. 26, 1977 and U.S. Pat. No. Re. 28,792, which reissued Apr. 27, 1976, the disclosures of which are incorporated herein by reference.

By coating the surface of the zirconium dioxide, or other solid electrolyte body with a catalytic material, such as platinum, a relatively high output signal can be generated whenever the combustion mixture is at an air/fuel ratio less than the stoichiometric mixture ratio for that fuel and a relatively low signal whenever the mixture is at an air/fuel ratio greater than the stoichiometric mixture ratio for that fuel. Thus, a generally step function will be generated by the sensor as the air/fuel mixture ratio passes through stoichiometry from a relative low to high value.

Typically, the solid electrolyte, as illustrated in the above referenced patents, is formed in the shape of a closed ended tube or a thimble. The thimble is coated on the inside and outside with a porous metallic electrode material, for example, platinum or palladium. The exterior of the closed end tube or thimble is inserted into the exhaust system and exposed to the heated exhaust gas created by the combustion of gases within an internal combustion engine, or is exposed to the incoming air/fuel mixture, while the interior of the close ended tube or thimble is exposed to atmospheric conditions. Thus, the sensor generates a voltage that is proportional to the difference between the partial pressures of oxygen between the interior and exterior of the electrolyte thimble.

The outside surface of the thimble is usually connected to an electrical ground through the attachment of the housing of the sensor to the exhaust system. The exhaust system in turn is connected to the chassis of the vehicle to form one of the conductors for a sensor. This type electrical ground connection is illustrated by a clip disclosed in U.S. Pat. No. 4,111,778.

Most vehicles use a multiplicity of electrical loads and as a result the electrical ground conductor for an oxygen sensor may have various electrical potential applied thereto and is practically never completely free of voltage variations. Unfortunately, the output signal as measured across the inner surface terminal of the sensor and outer surface terminal grounded to the vehicle may not be the true output from the sensor itself. The electrical loading characteristics and operational potential generated by the other electrical components of the vehicle may therefore change the actual voltage signal as measured in the sensor and could interfere with proper operation of the control system setting of the air/fuel mixture to be supplied to the combustion chamber. Thus, the composition of the exhaust gases being emitted from the engine could be adversely affected by this type of sensor construction.

U.S. Pat. No. 4,019,974 attempted to overcome this problem with a positive ground crimped to a terminal connected to the outside surface conductor. In this sensor, a resilient conductive mass of graphite is positioned around the thimble by a mass of insulating powder to provide an electrical path between the outside conductive surface and terminal connector. Unfortunately this structure requires some complicated and expensive manufacturing in order to maintain the components in their spacial relationship to assure that an adequate and uninterrupted electrical flow path is produced between the outside conductive surface and the electrical terminal.

When oxygen sensors are installed on vehicles they are often subjected to extreme environmental conditions. It is not uncommon for an oxygen sensor to be submerged in water as a vehicle travels through a stream or in a flooded roadway. The need to maintain a relative dry reference gas was recognized in the invention disclosed in U.S. Pat. No. 4,116,797 when a TEFLON filter was installed in the flow path to the reference chamber. Unfortunately this type seal construction does not positively seal when the components are subjected to rapid changes in temperature.

Oxygen sensors are normally located in the exhaust pipe of most vehicles. The normal temperature of exhaust gases is about 600° C. but under some circumstances the exhaust gas may reach 900° C. for a period of time. The oxygen sensor disclosed in U.S. Pat. No. 37,362 includes structure which allows for a positive ground to be supplied to both an electrochemical sensor and a heater. The leads for the sensor and heater which are connected to a control member and the ground pass through a porous filter and resilient seal. As long as the temperature in the sealing area is below 200° C. dry reference gas is presented to the electrochemical thimble member. However if the temperature experienced by the seal and filter is above 200° C. the differences in coefficient of expansion of the seal, filter and metal shell may result in a deformaion in either the seal or filter which would allow a leak path to develop for water to enter into the thimble. It has been determined that the continuous axial loading of the seal and filter in this sensor at the high temperature causes the seal to lose some resiliency and the porosity of the filter to be changed.

SUMMARY OF THE INVENTION

In order to simplify the structure of an oxygen sensor and eliminate axial loading of the seal and filter we have devised a method of manufacture whereby module components are systematically joined together to develop a heated electrochemical sensor having an isolated ground.

In this sensor, a tubular electrochemical thimble member is inserted into an isolated carrier member in a metal shell. The thimble has its internal and external surfaces coated with a conductive material. A sleeve has a closed end with a plurality of openings therein. A porous filter has an annular axial projection that extends from a base. A pleated type seal has a center that surrounds the axial projection. Thereafter the axial projection on the porous filter is inserted into an opening in the closed end and moved to bring the seal into contact with the closed end and lead wires are broght through the filter and seal. A first terminal is attached to a first wire connected to a power source in a control member and a second terminal is attached to a second wire to establish an electrical ground in the control member. Third and fourth wires are also carried through passages in a cylindrical member. A first contact ring is attached to the third wire and a second contact ring is attached to the fourth wire. The first contact ring is placed on an annular projection that extends from the cylindrical member and positioned on a first shoulder. A stepped axial bore extends through the projection into the cylindrical member. The second contact ring is placed in the stepped axial bore and positioned on a second shoulder. The annular projection in addition to electrically isolating the first and second contact rings forms a guide surface for a spring washer. The cylindrical member has first and second axial grooves located on its peripheral surface that extend to first and second radial offset slots. The radial slots extend at least into the stepped axial bore. The first and second terminal are thereafter pushed into the first and second radial slots, respectively. A tubular heater member inserted into the stepped axial bore has a first end with a first contact surface that engages the first terminal and a second contact that engages the second terminal. A coil spring is placed over the tubular heater and a contact cup located on the end of the coil spring. The contact cup has a series of prongs or projections that engage the surface of the tubular heater to hold the coil spring and position the tubular heater within the thimble of the sensor. A cylindrical contact extension has a first end with a flange thereon that is positioned on the annular projection of the terminal member. The heater is aligned with the interior of the tubular electrochemical member and a force is applied to bring a second end on the contact extension into contact with the internal surface of the carrier member while at the same time the contact cup is brought into engagement with the internal surface of the electrochemical sensor member. The spring washer and coil springs resiliently urge the terminal member away from the electrochemical sensor member to provide for an electrical flow path between the internal and external surfaces of the electrochemical member and the control member. A laser weld is formed around the sleeve surface to join and seal the sleeve to the metal shell. In an alternate construction, a portion of the sleeve may be rolled into a groove in the metal shell to seal the joint.

An advantage of this oxygen sensor is achieved through the individual assembly of various components that are later joined together in a final assembly.

A further advantage of this oxygen sensor resides in the terminal structure which carries leads to both an electrochemical sensor member and an internal heater associated therewith.

A still further advantage of this oxygen sensor occurs since the sleeve which carries the terminal structure has a sealed joint with respect to a metal shell and as a result a reference gas must pass through a porous filter that extends through the metal shell before entering into a reference chamber of an electrochemical member.

A further advantage of this invention resides in a seal and filter which is radially retained in a metal shell to allow axial expansion to take place during periods of exposure to high temperature without either seal or filter deformation occurring as a result of axial restraint.

A still further advantage of this oxygen sensor is provided through the electrical ground connection for both an electrochemical member and a heater are in a control member to assure that an operational signal generated thereon represents a true comparison of an oxygen component in a mixture of exhaust gases with a reference gas after being subjected to high temperature and exposure to water or other liquids over an extended period of time.

These advantages and others should be apparent from reading the specification while viewing the drawings wherein:

FIG. 1 is a schematic illustration of a vehicle engine with an electrochemical sensor, made according to this invention, located in an exhaust system to provide a fuel management system with an indication of the oxygen in exhaust gases; and FIG. 2 is a sectional view of the electrochemical sensor of FIG. 1; and FIG. 3 is a sectional view taken along line 3—3 of FIG. 2; and FIG. 4 is a sectional view taken along line 4—4 of FIG. 2; and FIG. 5 is a sectional view taken along line 5—5 of FIG. 2; and FIG. 6 is a perspective view of the terminal member of FIG. 2; and FIG. 7 is a perspective view of the terminal spade for the heater lead of FIG. 2; and FIG. 8 is a perspective view of the contact cup of FIG. 2; and FIG. 9 is an enlarged sectional view of the leads for the terminal spades and contact rings in FIG. 2; and FIG. 10 is an exploded view of the electrochemical sensor of FIG. 2 illustrating a method whereby the individual components are joined together into a final assembly; and FIG. 11 is a partial sectional view of an alternate seal between the metal shell and tubular sleeve for the sensor of FIG. 2; and FIG. 12 is an enlarged view of the elastomeric seal of FIG. 2 showing the convoluted surfaces on the openings therein and surfaces that contact surfaces on the metal shell;

FIG. 13 is an end view of the elastomeric seal of FIG. 12; and

FIG. 14 is an enlarged view of the porous filter for use with the elastomeric seal shown in FIG. 12.

DETAILED DESCRIPTION OF THE INVENTION

Figure 1:
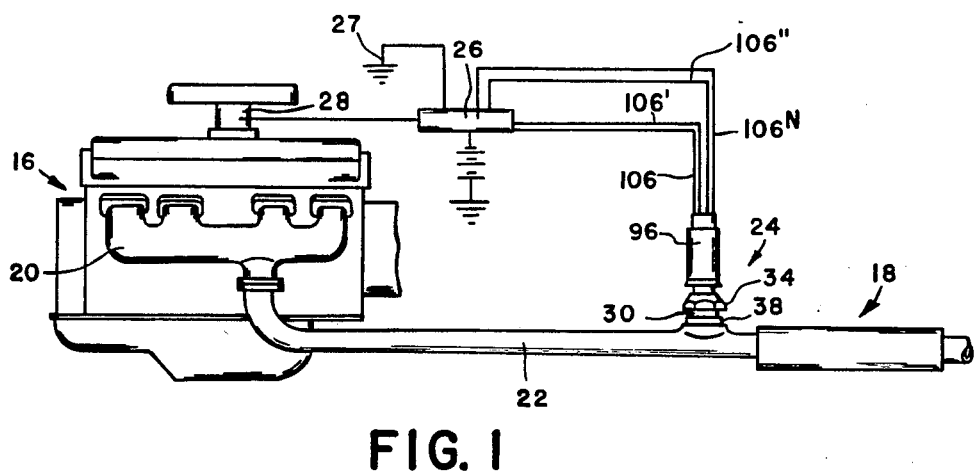
Figure 2:
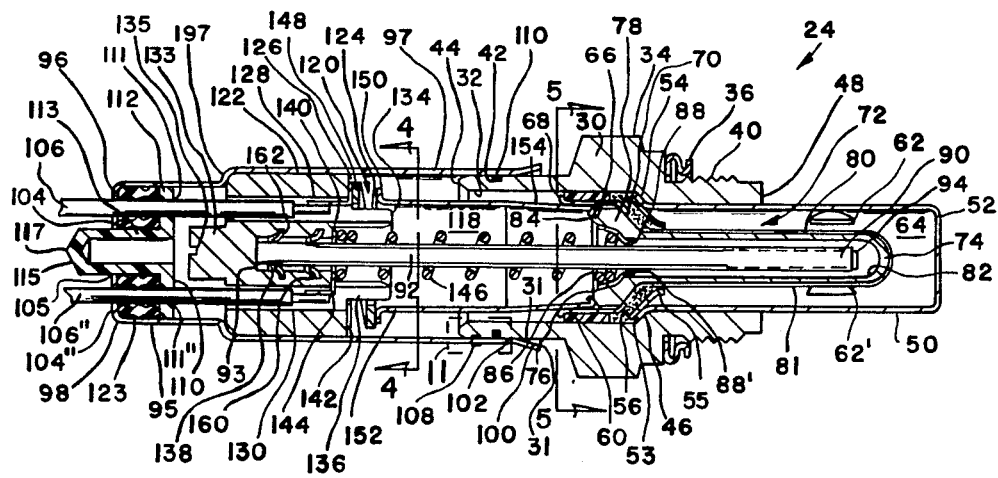
Figure 3:
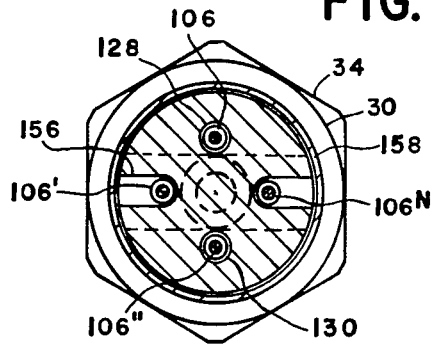
Figure 4:
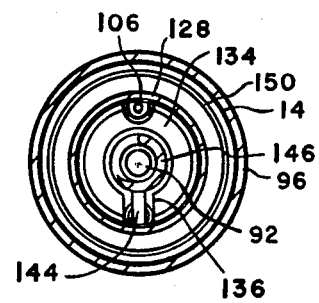

The internal combustion engine 16 shown in FIG. 1 has an exhaust 18 system through which exhaust gases are transmitted from manifold 20 through pipe 22 to the surrounding environment. An electrochemical sensor 24 located in pipe 22 supplies controller 26 with an indication of the oxygen content of the exhaust gases. The controller 26 provides an electronic fuel metering apparatus 28 with an operational signal to control the air/fuel ratio that is supplied to operate the engine 16.

Changes in the oxygen content in the exhaust gases are experienced by the electrochemical sensor 24 and transmitted to the controller 26 to maintain the air/fuel ratio signal to the metering apparatus 28 within set operational limits to provide for fuel economy in addition to meeting clean air standards. Both the positive and negative leads for sensor 24 are connected to the controller 26 to prevent any changes in the electrical ground within the vehicle from affecting the operational signal generated from the changes of the oxygen content in the exhaust gases.

The oxygen sensor 24 is shown in more detail in FIGS. 2-9 and 12-14. Sensor 24 has a metal shell 30 with an axial bore 32 therein. A hexagonal surface 34 has a washer 36 that engages boss 38 when threads 40 are screwed into corresponding threads in the exhaust pipe 22. Metal shell 30 has a peripheral groove 42 adjacent a first end 44 and an internal annular shoulder 46 located between the first end 44 and a second end 48 in the axial bore 32.

A vented shield 50 has a first end 52 and a second end 53. The second end 53 has flange 54. The vented shield 50 is inserted in the axial bore 32 and flange 54 seated on shoulder 46. A plurality of openings 62, 62' ... $62^n$ allow exhaust gases to be freely communicated into the interior 64 of the shield 50.

A support member 57 is placed in the axial bore 32 and engages flange 54. Thereafter a sealing and insulating ring 60, e.g. talc, is placed in the bore 32 adjacent flange 54 on the support member 57. An insulator spacer 56, a ceramic disc, is placed in the axial bore 32 and engages ring 60. Thereafter an element. Carrier 66 is located in bore 32, carrier 66 has a cylindrical body with a flange 68 on a first end and an inwardly projecting lip 70 on the other end. The cylindrical body of carrier 66 engages the insulator spacer 56 while lip 70 engages the talc ring 60.

The sensor element 72 is in the form of a tubular thimble and is made of an ion conductive solid electrolyte such as zirconium dioxide. The thimble has a closed end 74 and an opened end 76. An annular external rib 78 adjacent the opened end 76 engages the lip 70 on the carrier 66. The external surface 80 and internal surface 82 of sensor element 72 are coated with a porous, electron conductive layer (e.g. platinum) to form a catalyst for gases which will be presented to these surfaces.

A porous insulating protecting coating 81, e.g. spinal, is applied to the external surface 80. The internal and external surface coatings 80 and 82 are separated at the opened end 76 by an uncoated annular surface 84 to assure that separate electrical flow paths are established to permit ion flow through the thimble. The external conductive coating 80 contacts the carrier body 66 and extends the flow path past the insulator ring or spacer 56 and talc ring 60 while contact cup 86 as best shown in FIG. 8, is located adjacent the opened end 76 to extend the interior surface coating 82 while still maintaining the isolation between the interior and exterior coatings.

When an axial force is applied to the carrier 66, flange 68 compresses the talc ring 60 to form a seal between the metal shell 30 and exterior surface 80 on thimble 72.

The contact cup 86 as best shown in FIG. 8 has a series of fingers or prongs 88, 88' ... $88^n$ that extend from an annular base 87. Prongs 88, 88' ... $88^n$ engage tubular member 90 on a heater member 92 to hold the end 94 of the heater 92 in approximately the radial center of the interior of the thimble 72 as shown in FIG. 5.

A sleeve 96 has a closed end 98 and an opened end 100. The sleeve 96 may have a flare 102 on the opened end 100 and a plurality of openings 104, 104' ... $104^n$ and 105 in the closed end 98. A first diameter section 95 of sleeve 96 is offset from a second diameter section 97 by a shoulder 197. A laser weld 108 joins the sleeve 96 to the metal shell 30 to form a water and air tight seal adjacent the opened end 100.

A porous filter material 112 sold under the trade name of Zitex by Norton Chemplast, or an equivalent material which allows air to flow through while excluding water, shown in more detail in FIG. 14, is located in sleeve 96. Filter 112 has an annular base 110 with a plurality of openings 111, 111' ... $111^n$ and an axial projection 113 that extends through opening 105. Projection 113 has a closed end 115 that terminates in an apex 117. A rubber seal 123 as best shown in FIGS. 12 and 13 is located between end 98 of sleeve 96 and the filter 123. Seal 123 has a central opening 205 and a series of axial openings 204, 204' ... $204^n$ which correspond with a series of axial openings 111, 111' ... $111^n$ in filter 112 and openings 104, 104' ... $104^n$ in the end 98. Lead wires 106, 106' ... $106^n$ extend through the openings 104, 104' ... $104^n$, 204, 204' ... $204^n$ and 111, 111' ... $111^n$ into the interior of the sleeve 96. The rubber seal 123 has a series of pleats 206, 206' ... $206^n$ on its peripheral surface and a series of pleats 208, 208' ... $208^n$ on its inner surface or opening 205. In addition similar pleats are located in openings 204, 204' ... $204^n$ which form a series of sealing surfaces with the leads 106, 106' ... $106^n$, the interior of sleeve 96 and projection 113 on filter 112. Seal 123 which is located between end 98 and the filter 112 has sufficient radial resiliency to form a tight seal with the sleeve 96 and the insulating coating on leads 106, 106' ... $106^n$ such that reference air is essentially only communicated through that portion of projection 113 that extends through opening 105. Because of the physical properties of filter 112 only dry reference air is presented to chamber 118.

A terminal member 120, as best shown in FIGS. 2, 3, 6 and 10, has a first diameter section 122 separated from a second diameter section 124 by a shoulder 126. An axial projection 133 extends from the first diameter. A slot 135 is located on the end of projection 133 to provide a flow path under conditions that may bring base 110 into engagement with the end of projection 133. First and second axial passages 128 and 130 extend from a first end 132 to a second end 134. A blind axial stepped bore 138 extends from the second end 134 toward the first end 132. An axial slot 136 in the terminal member 120 extends from the second end 134 to a shoulder 140. A first contact ring 142 attached to lead 106 is located on shoulder 140. A coil spring 146 which surrounds tubular heater 92 and forms an electrical flow path between contact ring 144 and cup 86. A spring washer 148 surrounds the second diameter section 124 and acts on contact ring 142 and flange 150 on carrier extension member 152. Carrier extension member 152 has a taper 154 on the end thereof which engages both the interior of carrier 66 and the opened end 76 of thimble of sensor element 72. Spring washer 148 provides for an electrical flow path whereby the external conductive surface 80 on sensor 72 is connected to lead 106.

Terminal member 120 has first and second grooves 156 and 158 on the periphery of the first diameter section 122 that extend to a first radial slot 160 that extends along a diameter which is at substantially a right angle to a plane through passages 128 and 130. A second slot 162 is parallel to the first slot 160. Slots 160 and 162 while shown extending clear through the first diameter section 122 may under some circumstances only extend to bore 138. Under normal operating conditions grooves 156 and 158, and slots 160 and 162, holes 128 and 130 act as flow paths for the communication of air from filter 112 into chamber 118.

Terminal or contact member 164, see FIG. 7, has a flat surface 166 with a leg 168 extending therefrom. A central opening 170 is located on the flat surface 166 and has prongs or fingers 172, 172' . . . 172$^n$ that extend therefrom. Lead wires 106' is attached to leg 168 and flat surface 166 is inserted into slots 160. When leg 168 engages the bottom of groove 156, opening 170 is located in the axial center of stepped bore 138. Similarly lead wire 106$^n$ is attached to a second terminal 164' and inserted into slot 162. When leg 168' engages the bottom of groove 158, opening 170' is located in the radial center of stepped bore 138.

Figure 10:
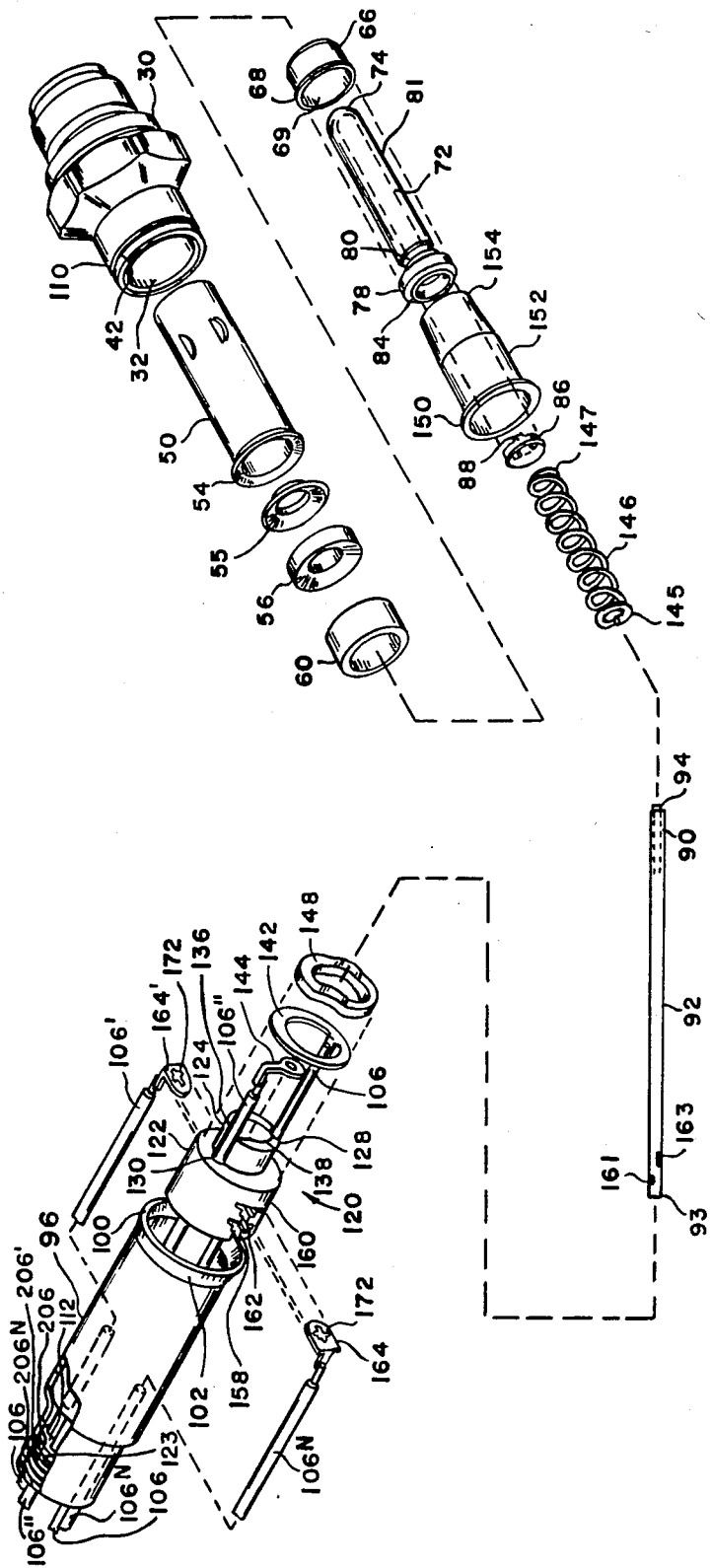

Heater 92, which is of the resistance type, has a first contact area 161 and a second contact area 163 as shown in FIG. 10. When end 93 of the tubular member 90 of heater 92 engages the bottom 139 of bore 138, the first contact area 161 engages prongs 172, 172' . . . 172$^n$ on terminal 164' and the second contact area 163 engages prongs 172, 172' . . . 172$^n$ on terminal 164 to complete an electrical circuit from controller 26. In addition to establishing an electrical circuit for heater 92, the prongs on terminal 164 and 164' resiliently engage the tubular member 90 to hold end 94 at desired position with respect to end 74 of the thimble of sensor 72.

Each of the leads 106, 106' . . . 106$^n$ is made up of several strands of individual wires. As shown in FIG. 9, at first group of wires 174 are wound in a clockwise direction while a second group of wires 176 are wound in a counterclockwise direction. As can be seen, a spiral space is formed between the first and second wires 174 and 176. A plastic cover 178 is placed on the outside of the wires 176 to prevent an electrical short from affecting transmission between the controller 26 and sensor 24. Further, this spiral space between the wires 174 and 176 provides an additional flow path for the communication of air (reference gas) to chamber 118.

METHOD OF ASSEMBLY OF THE INVENTION

The exploded view of sensor 24 seen in FIG. 10 illustrates a preferred method of assembly of the individual component parts to create the heated and externally grounded electrolyte sensor for use in determining the oxygen content in the exhaust of an internal combustion engine.

In this assembly, a metal shell 30 is selected from a supply and a vented shield 50 is inserted in bore 32 in shell 30 until flange 54 engages shoulder 46. A support 57 is inserted in bore 32 and positioned against flange 54. A talc sealing ring 60 is placed in bore 32 adjacent support member 57 and an insulating ring 56 placed on the talc sealing ring 60.

A first carrier member 66 is then inserted in bore 32 and flange 68 brought into engagement with the insulating ring 56. A tool is inserted into bore 32 and acts on flange 68 and rib 78 to compress the talc ring and establish a seal between the thimble 72, metal shell 30 and carrier 66. Under some circumstances metal gasket may be required between rib 78 and lip 70 to form a good electrical connection and gas seal between surface 30 and carrier 66.

The closed end 74 of sensor element 72 is inserted into carrier member 66. External rib 78 engages the interior surface 69 of carrier member 66 to form an electrical connection with the external surface coating 80.

Thereafter a carrier extension member 152 is located in bore 32 and forced into surface 69 on carrier member 66 until it engages rib 78 on the sensor 72.

The assembly of the terminal end of the sensor element 24 starts by pulling leads 106, 106' . . . 106$^n$ through openings 104, 104' . . . 104$^n$ in closed end 98 of sleeve 96, openings 204, 204' . . . 204$^n$ in rubber seal 123 and openings 111, 111' . . . 111$^n$ in filter 112. The seal 123 and filter 112 are pushed into engagement with end 98. The pleated surfaces 206, 206' . . . 206$^n$ have sufficient radial resiliency to form a tight seal with the interior of sleeve 96. When seal 123 engages end 98, projection 113 extends through opening 105 to be exposed to the surrounding envronment.

A first terminal 164 is attached to the end of lead wire 106' and a second terminal 164' is attached to lead wire 106$^n$.

Leads 106 and 106" are pulled through passages 128 and 130 in terminal member 120 and contact rings 142 and 144 attached thereto. Lead 106" is pulled to seat contact ring 144 on shoulder 140 in bore 138. Similarly lead 106 is pulled to seat contact ring 142 onto shoulder 126.

The first terminal 164 is inserted into slot 160 and the second terminal 164' is inserted into slot 162.

End 93 of tubular heater 92 is inserted in bore 138 and is resiliently engaged by prongs on terminals 164 and 164'. When end 93 contacts the bottom 139 of bore 138, surface areas 161 and 163 on tubular member 90 will be in contact with prongs 172 of terminals 164 and 164' to form a complete electrical current with leads 106' and 106$^n$. Thereafter, wave or washer spring 148 is placed on cylindrical surface 124 and positioned adjacent contact ring 142.

Coil spring 146 is placed over the tubular member 90 and end 145 brought into engagement with contact ring 144. A contact cup 86 is placed on the tubular surface 90 and brought into position adjacent end 147 of the coil spring 146. Prongs 88 on cup 86 resilient engage the tubular surface so that the coil spring does not fall off if the terminal section is placed in a vertical position with the heater member 92 pointing toward the ground.

We now have essentially two individual assemblies which are to be joined together to produce sensor 24.

Sleeve assembly 96 and shell assembly 30 are brought together as end 94 on heater 92 is aligned with bore 81 of the thimble sensor 72. Contact cup 86 engages the interior surface of the opened end 76 of the sensor 72 and sleeve 96 engages end 42 of metal shell 30 as end 94 is moved into bore 81. A predetermined force, which moves the sleeve 96 and shell 30 together, is maintained while a laser moves around the sleeve 96 to join the parts together. As these parts are moved together, spring washer 148 acts on carrier extension 152 to hold tapered end 154 into engagement with surface 69 of carrier 66 and link external conductive coating 80 on the thimble of sensor 72 with the negative lead 106 to controller 26. At the same time spring 146 moves contact cup 86 into engagement with the interior conductive surface 82 to provide a link with the positive lead 106" to controller 26.

METHOD OF OPERATION OF THE INVENTION

When the internal combustion engine 16 is operating, exhaust gases are produced and carried by pipe 22 to the environment. With sensor 24 installed in pipe 22, the exhaust gases are communicated through openings 62, 62' in shield 50 to chamber 64.

Air from the environment is carried through projection 113 of filter 112 to chamber 118 and to the interior coating 82 of the thimble of sensor 72.

Electrical current from controller 26 is carried on leads 106' and $106^n$ to heater member 92. The resistance of heater member 92 is such that the temperature of the thimble is maintained above its minimum operating temperature which for zirconium dioxide is above 350° C.

With changes in the ion flow between exterior conductive surface 80 and interior conductive surface 82, an operational signal is carried on lead 106 to controller 26. Since lead 106" is electrically grounded through controller by an isolated ground, the operational signal is an accurate measure of a change in ion flow. The controller 26 evaluates the ion flow signal and generates an operational signll which controls the air/fuel ratio supplied to engine 16 to maintain the exhaust gases within desired operational standards.

Under operating conditions the temperature that is Presented to the shell can reach 400° C. which causes the components to expand. The pleated shape of seal 123 allows expansion to take place as the filter 112 moves toward stop 133 on terminal member 120. The plurality of pleats or surfaces 206,206' . . . $206^n$ assures that a surface will radially engage the interior of surface 105 even if a lateral force on lead 106,106' . . . $106^n$ should exert a force that may pull one of the pleats or surfaces away from its radially sealing engagement with surface 95. The length of projection 113 is such that surface 115 extends through opening 105 when base 110 engages stop 133. Even with such engagement the reference air is still communicated to chamber 118 by way of bore 119, slot 135 and grooves 156 and 158. When the exposure to high temperature terminates, seal 123 returns to its original shape without any permanent deformation and the porosity of filter 112 is substantially unchanged since it has not been subjected to axial forces that could cause compression of the pores size.

In actual test the filter 112 and seal 123 were exposed to a temperature of 250° C. for a time period and were thereafter submerged in a tank of water for a time period of 1 hour. Thereafter the chamber 118 was checked for water and none was found. Further the operation of the sensor 24 was found to correspond to its operation prior to this severe test.

We claim:

1. In an oxygen sensor having a solid electrolyte member located in a metal shell and a terminal member located in a sleeve attached to the metal shell, the terminal member retaining first and second contacts on corresponding leads which connect the solid electrolyte member to a controller and third and fourth contacts on corresponding leads which connect a heater associated with the electrolyte member with the controller, said sleeve having an end with a plurality of openings for said leads and a central opening, said central opening allowing environmental air to be communicated to a reference chamber between the terminal member and solid electrolyte, the improvements comprising:

a filter having a base member in radial engagement with the sleeve and an axial projection that extends from the base member through said central opening in said end of said sleeve into the surrounding environment, said filter allowing environmental air to be communicated to said reference chamber while excluding water; and a seal member having an inner and outer periphery, said outer periphery having a first series of pleats that radially engage said sleeve; said inner periphery having a second series of pleats that radially engage said axial projection on said filter, said seal member having a series of opening for said leads, said openings in said seal member having a third series of pleats that engage said leads to prevent environmental air from being communicated through said openings in said seal member to assure that environmental air presented to said reference chamber passes through said axial projection of said filer, said solid electrolyte member being exposed to exhaust gases from a vehicle while said reference chamber is presented with substantially dry environmental air through said filter, said heater maintaining said reference chamber above a preset temperature such that changes in the oxygen content in the exhaust gases as compared to oxygen in the reference environmental air cause ions to flow in the electrolyte member, said changes in ion flow being presented to the controller through said first and second contacts, said seal member axially expanding in response to temperature while retaining said radial engagement with said sleeve and said axial projection on said filter to assure that only dry environmental air is communicated to said reference chamber.

2. In the oxygen sensor as recited in claim 1 wherein said filter moves as said seal member expands and engages a stop on said terminal member, said stop having a slot that assures the communication of dry environmental air to the reference chamber is not interrupted.

3. In the oxygen sensor as recited in claim 2 wherein as said leads connected to the first, second, third and fourth contacts pass through said seal member and exert a lateral force on a portion of said seal member said series of pleats on said inner and outer periphery maintain radial contact with said sleeve and axial projection as a result of such lateral forces to assure that a seal is retained.

4. In the oxygen sensor as recited in claim 3 wherein said axial projection on said filter extends through said end of said sleeve when said base member engages said stop to assure that the environmental air is communicated to the filter outside of said sleeve.

5. In the oxygen sensor as recited in claim 4 wherein axial movement of said seal member and filter by temperature does not cause any permanent deformation.

* * * * *